United States Patent [19]

Powell et al.

[11] Patent Number: 4,942,247

[45] Date of Patent: Jul. 17, 1990

[54] ORGANIC NITRILES AS INSECT ANTIFEEDANTS

[75] Inventors: Richard G. Powell, Peoria, Ill.; Kenneth L. Mikolajczak, Belleair Bluff, Fla.; Bruce W. Zilkowski, Peoria, Ill.; Jon Clardy, Ithaca, N.Y.; Ellen K. Mantus, Ithaca, N.Y.

[73] Assignees: The United States of America as represented by the Secretary of Agriculture, Washington, D.C.; Cornell Research Foundation, Inc., Ithaca, N.Y.

[21] Appl. No.: 371,879

[22] Filed: Jun. 27, 1989

[51] Int. Cl.[5] ........................................... C07D 209/10

[52] U.S. Cl. .................................... 548/505; 558/388

[58] Field of Search ......................... 548/505; 558/388

[56] References Cited

PUBLICATIONS

Marchand et al., "Sulfenylation of Nitriles by Elemental Sulfur in a Basic Medium: Preparations of alpha-Cyano Sulfides, Disulfides, and Dithioacetals" C. R. Hebd. Seances Acad. Sci. Ser. C, 289(2): 57-60 (1979); Abstract, CA 92, P616 (1980).

Dahiya and Rimmer, "Phytoalexin Accumulation in Tissues of *Brassica napus* Inoculated with *Leptosphaeria maculans,*" Phytochemistry 37(10): 3105-3107 (1988).

*Primary Examiner*—Mary C. Lee
*Assistant Examiner*—Jacqueline Haley
*Attorney, Agent, or Firm*—M. Howard Silverstein; John D. Fado; Mervin E. Brokke

[57] ABSTRACT

Members of a novel class of organic nitriles related to an indole alkoaloid of *Dithyrea wislizenii* (Cruciferae) have been discovered to be potent feeding inhibitors of the fall armyworm and European corn borer.

10 Claims, No Drawings

ORGANIC NITRILES AS INSECT ANTIFEEDANTS

BACKGROUND OF THE INVENTION

1. Field of the Invention

This invention relates to a novel class of organic nitriles which exhibit potent antifeeding activity toward the fall armyworm, *Spodoptera frugiperda* (J. E. Smith), and European corn borer, *Ostrinia nubilalis* (Hübner).

2. Summary of the Prior Art

Allomones are described by Schoonhoven [In Semiochemicals, Donald A. Nordlun, Richard L. Jones, and W. Joe Lewis (eds.), p. 31 ff., John Wiley & Sons (1981)] as chemical mediators produced by plants which protect them from insects. Allomones may or may not be toxic to insects, but they deter or inhibit the feeding of insects on the plant by activating deterrent sensitive receptors in the insect.

The search for natural pest control agents has extended into many plant species and resulted in the isolation and, in some cases, identification of feeding deterrents or allomones of varied chemical structure.

For example, Mikolajczak and Reed reported the study of 22 species of plants from the Meliaceae family [J. Chem. Ecol. 13(1): 99 (1987); see also Mikolajczak et al., J. Chem. Ecol. 15(1): 121 (1989)]. Seed extracts were tested for antifeedant activity and toxicity against the fall armyworm and striped cucumber beetle. A number of the extracts were comparable in activity to neem preparations which contain azadirachtin, a semi-commercial allomone [see J. D. Warthen, Jr., USDA Agricultural Reviews and Manuals, ARM-NE-4, 21 pp. (1979)].

Kubo et al. [J. Chem. Soc., Chem. Commun. 1976: 1013 (1976)] isolated potent armyworm antifeedants from East African Warbergia plants. These were characterized as bicyclic dialdehyde structures polygodial, ugandensidial, and warberganal.

Myricoside, another armyworm antifeedant, was reported to be a complex polycyclic compound by Cooper et al. [J. Am. Chem. Soc. 102(27): 7953 (1980)].

Mikolajczak and Weisleder [J. Nat. Prod. 51(3): 606 (1988)] isolated a limonoid antifeedant for the fall armyworm.

Certain indole compounds are known to exert biological effects upon insects. Smissman et al. [Science 133: 462 (1961)] reported that indole-3-acetonitrile which was isolated from cabbage plants inhibited the growth of *Pyrausta mibelalis* (Hbn.). Indole-3-acetic acid, a closely related structure, did not inhibit insect growth under the same assay conditions.

Luis J. Corcuera [Phytochemistry 23(3): 539–541 (1984)] found that several indole alkaloids from Gramineae showed feeding deterrent activity on aphids at low concentrations. These compounds are 3-N,N-dimethylaminomethylindole derivatives.

Takasugi et al. [Bull. Chem. Soc. Jpn. 61: 285 (1988)] and Dahiya and Rimmer [Phytochemistry 27(10): 3105 (1988)] have reported the isolation of sulfur-containing indole phytoalexins from the Chinese cabbage.

Phenyl-dimethylmercaptoacetonitrile, compound 10 of this invention, was previously prepared by Marchand et al. [C.A. 92: P616 (1980)]; no biological activity of any sort was reported for this material.

SUMMARY OF THE INVENTION

It is an object of this invention to described a new class of biologically active organic nitriles.

A further object of the invention is to teach a method of inhibiting feeding of insects by applying an organic nitrile to the food of the insect.

Additional objects of the invention will be set forth in the description which follows, and will become apparent to those skilled in the art upon examination of the specification or by practice of the invention.

DETAILED DESCRIPTION OF THE INVENTION

We have now discovered a previously unrecognized class of organic nitriles, that are potent feeding inhibitors of insect species.

The first example of this new group of compounds was isolated from an extract of *Dithyrea wislizenii* (Cruciferae). The structure was determined to be 3-(dimercaptomethyl-cyanomethyl) 7-methoxy indole (also named dithyreanitrile). This new indole alkaloid derivative inhibits feeding of fall armyworm (*Spodoptera frugiperda*) and European corn borer (*Ostrinia nubilalis*) larvae and is the first example of a natural product having two sulfur atoms and a nitrile group bonded to the same carbon atom. The structure of dithyreanitrile was determined by $^{1}H$ NMR, $^{13}C$ NMR, mass spectrometry, and X-ray crystallography and confirmed by synthesis.

The Cruciferae family is well known as a major source of nitrile and sulfur-containing secondary metabolites [Fenwick et al., CRC Crit. Rev. Food Sci. Nutr. 18: 123 (1983)]. These compounds are responsible for the characteristic odors and flavors of common spices and vegetables such as mustard, cabbage, radish, and broccoli. Many of these same compounds are also known to produce a broad variety of physiological responses in, or inhibit the growth of, plants, animals, insects, and microorganisms [Fenwick et al., supra; Takasugi et al., J. Chem. Soc., Chem. Commun. 1986: 1077 (1986); Wall et al., J. Nat. Prod. 51: 129 (1988)]. However, dithyreanitrile appears to be the first example of a natural product having two sulfur atoms and a nitrile group bonded to the same carbon atom.

An extract of *Dithyrea wislizenii* (Engelm.) seed was investigated to discover new naturally occurring compounds with potential for control of insects. *D. wislizenii*, a member of the Cruciferae family, is native to the southwestern United States and northern Mexico.

Antifeedant activity-directed isolation was accomplished by steeping ground *D. wislizenii* seed with $H_2O$/EtOH, partitioning the extract with hexane to remove lipids, evaporating the aq EtOH solubles to dryness, and partitioning the residue between $Et_2O$ and $H_2O$. The $Et_2O$ solubles were then subjected to column chromatography, prep. tlc, and hplc on silica, yielding crystalline dithyreanitrile (8).

Dithyreanitrile was obtained as an off-white crystalline solid having a molecular formula $C_{13}H_{14}N_2OS_2$ as indicated by mass measurement and by an off-resonance decoupled $^{13}C$ NMR spectrum. The chemical ionization mass spectrum exhibited an ion at m/z 281 ($MH^{+}+2$), consistent with two sulfur atoms, and had major ions at m/z 252 ($MH^{+}$-HCN) and 231 ($MH^{+}$-$CH_3SH$). Proton NMR indicated the presence of two equivalent S-methyl groups ($\delta 2.28$), one O-methyl group ($\delta 3.95$), three adjacent aromatic protons, and one additional aromatic proton coupled only to an exchangeable proton (NH, δ8.44). A strong signal at δ15.7 in the $^{13}C$ spectrum also indicated the presence of two identical S-methyl groups. Spectral data are fully consistent with the structure which was determined by X-ray crystallography.

The structure of dithreanitrile was also confirmed by chemical synthesis as shown in the formulae below.

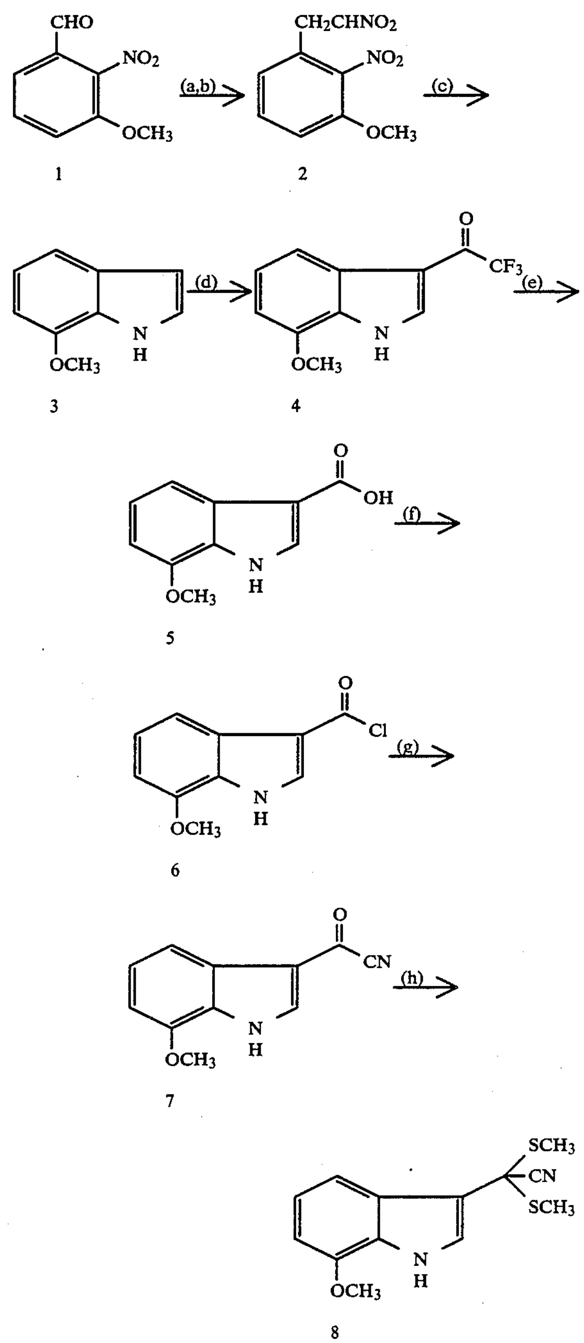

(a)$CH_3NO_2$, NaOH, $CH_3OH$;
(b)$(CH_3CO)_2O$, $CH_3CO_2^-Na^+$, reflux;
(c)$H_2$, 10% Pd/C, $CH_3CO_2CH_2CH_3$, $CH_3CO_2H$;
(d)$(CF_3CO)_2O$, $Et_2O$;
(e)NaOH, EtOH, reflux;
(f)$(COCl)_2$, $CH_2Cl_2$;
(g)TMS-CN;
(h)TMS-$SCH_3$, $(C_2H_5)_2O.BF_3$, $Et_2O$.

Compound 8, dithyreanitrile, was found to be identical in all respects with the material isolated from *Dithyrea wislizenii.*

Compounds related to dithyreanitrile were prepared by standard synthetic methods and found to be effective antifeedants for insects, especially for armyworms and corn borers. The present invention comprises compounds of the general formula:

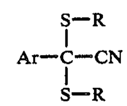

wherein R is alkyl and Ar is an aromatic ring system such as phenyl or indolyl. The aromatic ring may be unsubstituted, monosubstituted, or polysubstituted with halogen, alkyl, alkoxy, and halogenated alkyl groups.

In general, the appropriately substituted aromatic acid is converted to the acid chloride and then to the corresponding aroyl cyanide by standard procedures. These intermediates may be isolated and purified or they may be used without purification as in Example 11. The final products may be prepared by reaction of the aroyl cyanide with alkylthiotrimethylsilane as in Example 11 and isolated by standard procedures. It will be obvious to those skilled in this art that other synthetic procedures may be used to prepare the compounds of this invention.

Examples of the structure of compounds of this invention are shown below.

Structures 8-17

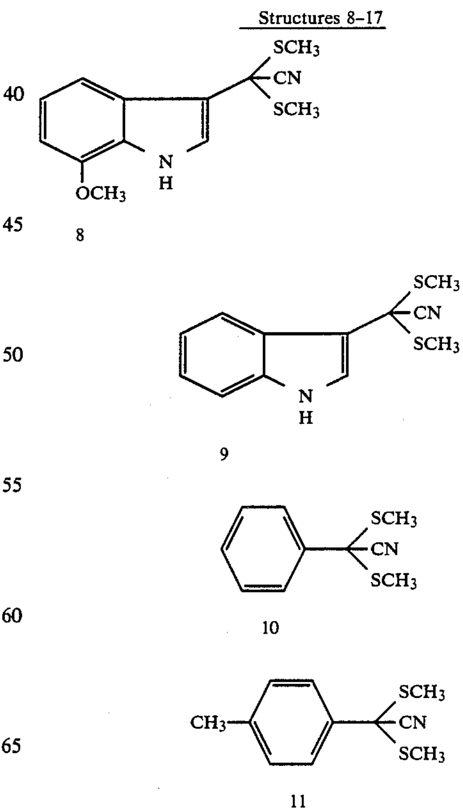

-continued

Structures 8-17

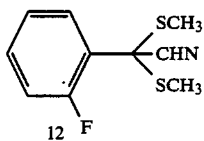

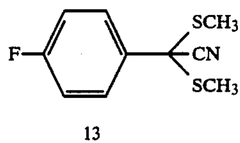

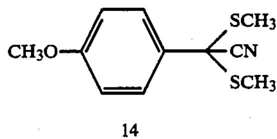

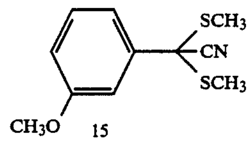

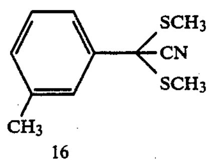

SCH3
CN
SCH3

17

Compounds were tested for antifeeding activity using a two-choice antifeedant bioassay. Results of these assays are reported in Tables I-IV. Nitriles of this invention were found to inhibit the feeding of insects when applied to the food at rates of 2400 ppm to 9.375 ppm.

As a practical matter, it is envisioned that commercial formulations of the subject antifeedant compounds might be prepared from plant extracts in the case of dithyreanitrile or from the pure synthetic materials.

The potency of these materials dictates that they be applied with a suitable inert carrier or vehicle as known in the art. Examples of suitable formulations are wettable powders and emulsifiable concentrates. Depending on the target species, substrate, and mode of application, the concentration of the compounds in the final composition may vary considerably but typically should be at least 300 ppm.

The compound is applied to the insects' food supply in an amount to inhibit feeding, as predetermined by routine testing. An effective amount is defined to mean the quantity of compound that will result in a significant reduction of feeding rate of a test group as compared to an untreated group. The actual effective amount may vary with the species of pest, the nature of the substrate, the type of vehicle or carrier, the period of treatment, and other related factors.

To be effective, the allomone must be applied to the insect food supply that is to be protected from the insect. In the case of plants, for example, the compound will typically be applied to the leaf surfaces.

The allomones encompassed herein are effective in inhibiting the feeding of a variety of insects. Without desiring to be limited thereto, pests of particular interest known to be vulnerable to treatment are agronomically important insects, especially armyworms and corn borers.

TABLE I

Organic Nitriles
Feeding Ratios: Armyworms
Feeding ratio = number of larvae on treated disks/number of larvae on control disks.
Number of larvae used to determine data points ranged from 55-95. Significant differences are indicated by *, , and * for the .05, .01, and .001 levels, respectively.

| | Sample Amount (ppm) | | | | | | | | |
|---|---|---|---|---|---|---|---|---|---|
| Compound | 2400 | 1200 | 600 | 300 | 150 | 75 | 37.5 | 18.75 | 9.375 |
| 8 | .08*** | .10*** | .15*** | .26*** | .49*** | .49*** | .51** | .77 | .96 |
| 9 | .03*** | .06*** | .14*** | .31*** | .53** | .66 | 1.24 | .85 | .76 |
| 10 | .07*** | .09*** | .12*** | .32*** | .50** | .61* | .67 | .89 | .73 |
| 11 | .02*** | .02*** | .10*** | .28*** | .41*** | .53** | .84 | .67 | .94 |
| 12 | .02*** | .03*** | .08*** | .22*** | .36*** | .33*** | .51*** | .59* | 1.03 |
| 13 | .09*** | .27*** | .74 | .97 | .93 | 1.22 | 1.10 | 1.10 | .67 |
| 14 | .02*** | .02*** | .04*** | .21*** | .24*** | .52** | .72 | .85 | 1.30 |
| 15 | .05*** | .02*** | .23*** | .67 | .75 | 1.08 | .58* | .70 | .91 |
| 16 | .00*** | .00*** | .02*** | .20*** | .18*** | .24*** | .30*** | .24*** | .32*** |
| 17 | .20*** | .32*** | .49** | .71 | 1.05 | .69 | 1.12 | .98 | .96 |

TABLE II

Organic Nitriles Range of Repellency Armyworms
Strong repellency is defined as feeding ratio of .10 or less; moderate repellency is defined as feeding ratio between .10 and 65; no repellency is when feeding ratio is .65 or greater.

| Compound | Strong Repellency (ppm) | Moderate Repellency (ppm) | No Repellency (ppm) |
|---|---|---|---|
| 8 | ≦1200 | 600 - 37.5 | ≧18.8 |
| 9 | ≦1200 | 600 - 75 | ≧37.5 |
| 10 | ≦600 | 300 - 75 | ≧37.5 |
| 11 | ≦600 | 300 - 75 | ≧37.5 |
| 12 | ≦600 | 300 - 18.8 | ≧9.4 |
| 13 | ≦2400 | 1200 | ≧600 |
| 14 | ≦600 | 300 - 75 | ≧37.5 |
| 15 | ≦1200 | 600 | ≧300 |
| 16 | ≦600 | 300 - 9.4 | ≧4.7 |
| 17 | ≦2400 | 2400 - 600 | ≧300 |

TABLE III

Organic Nitriles
Feeding Ratios: Corn Borers
Feeding ratio = number of larvae on treated disks/number of larvae on control disks. Number of larvae used to determine data points ranged from 55–95. Significant differences are indicated by *, *, and * for the .05, .01, and .001 levels, respectively.

| | Sample Amount (ppm) | | | | |
|---|---|---|---|---|---|
| Compound | 2400 | 1200 | 600 | 300 | 150 |
| 8 | .53** | .69 | .75* | .88 | .83 |
| 9 | .11*** | .24*** | .55** | 1.16 | .80 |
| 10 | .11*** | .17*** | .72 | .81 | .87 |
| 11 | .45** | .81 | 1.27 | 1.02 | 1.28 |
| 12 | .15*** | .68 | 1.36 | 1.17 | 1.43 |
| 13 | .09*** | .52** | 1.02 | 1.00 | 1.00 |
| 14 | .47*** | 1.24 | 1.22 | .74 | 1.15 |
| 15 | .07*** | .51** | 1.05 | 1.05 | .94 |
| 16 | .42*** | .64* | .98 | 1.09 | .96 |
| 17 | .74 | .65 | .93 | .86 | 1.07 |

TABLE IV

Organic Nitriles
Range of Repellency for Corn Borers
Strong repellency is defined as feeding ratio of .10 or less; moderate repellency is defined as feeding ratio between .10 and .65; no repellency is when feeding ratio is .65 or greater.

| Compound | Strong Repellency (ppm) | Moderate Repellency (ppm) | No Repellency (ppm) |
|---|---|---|---|
| 8 | <2400 | 2400 | ≧1200 |
| 9 | <2400 | 2400 - 600 | ≧300 |
| 10 | <2400 | 2400 - 1200 | ≧600 |
| 11 | <2400 | 2400 | ≧1200 |
| 12 | <2400 | 2400 | ≧1200 |
| 13 | ≦2400 | 1200 | ≧600 |
| 14 | <2400 | 2400 | ≧1200 |
| 15 | ≦2400 | 1200 | ≧600 |
| 16 | <2400 | 2400 - 1200 | ≧600 |
| 17 | <2400 | <2400 | ≧2400 |

The following examples are intended only to further illustrate the invention and are not intended to limit the scope of the invention which is defined by the claims.

EXAMPLE 1

Plant Material and Extraction

Seeds of *Dithyrea wislizenii* (Engelm.), stored at the Northern Regional Research Center, Peoria, Ill., under the identifier NU46313, were collected and authenticated by USDA botanists, Beltsville, Md. Ground *D. wislizenii* seed, 4.8 kg, was steeped for 24 hrs in $H_2O$/EtOH (1:4). Solvent was then removed and the procedure repeated two more times. Solvent collections were combined and the aqueous layer was partitioned three times with hexane (200 mL of n-hexane per 800 mL of $H_2O$/EtOH). The hexane layers were combined and evaporated to yield 78 g of oil, and the aq EtOH layer was evaporated to dryness, yielding 263 g of residue. This residue was partitioned between $Et_2O$ and $H_2O$, yielding 44 g of $Et_2O$ soluble material; the latter was repellent to fall armyworms, using the leaf disc antifeedant bioassay.

EXAMPLE 2

Fractionation of Extract

The $Et_2O$ soluble material obtained by solvent partitioning was chromatographed, batchwise, on a 70×2.3 cm glass column packed with silica gel. Eluting solvents were: $CHCl_3$, 1% MeOH in $CHCl_3$, 2% MeOH in $CHCl_3$, 3% MeOH in $CHCl_3$, 4% MeOH in $CHCl_3$, 8% MeOH in $CHCl_3$, 15% MeOH in $CHCl_3$, and 25% MeOH in $CHCl_3$. The "active" compound eluted prior to the 4% MeOH in $CHCl_3$. Fractions enriched in the active compound (570 mg) were subjected to HPLC in 100% $CHCl_3$ using a Whatman partisil 10 PAC 20 Magnum column, a Waters model 590 HPLC system, and a Waters 410 differential refractometer detector. Final purification was accomplished on a Rainin Dynamax Macro 12" silica column using $CHCl_3$ as the eluting solvent. This procedure yielded 44 mg of dithyreanitrile.

EXAMPLE 3

Mass Spectra Data for Dithyreanitrile $C_{13}H_{14}N_2OS_2$, mp 135° (sharp). Mass spectra were obtained with a Finnigan MAT 4535/TSQ instrument: EI mass spectrum (70 eV) m/z (rel. int.) $[M]^+$278 (2), 231 (100), 216 (14), 185 (12); CI mass spectrum (argon) m/z (rel. int.) $[MH+2]^+$281 (1), $[MH]^+$279 (11), $[MH-HCN]^+$252 (96), $[MH-CH_3SH]^+$231 (100), 206 (20), 185 (7).

EXAMPLE 4

NMR Data for Dithyreanitrile

NMR spectra were obtained with a Bruker WM-300 WB spectrometer. $^1H$ NMR (300 MHz, $CDCl_3$) $\delta$2.28s (6H, 2×$SCH_3$), 3.95s (3H, $OCH_3$), 6.69d (H-4, $J_{4,5}=7.9$ Hz), 7.09 m (H-5, $J_{4,5}=7.9$, $J_{5,6}=8.3$ Hz), 7.45d (H-2, $J_{1,2}=3.0$ Hz), 7.66d (H-6, $J_{5,6}=8.3$ Hz), 8.44br s (NH). $^{13}C$ NMR (75.5 MHz, $CDCl_3$) $\delta$15.7 (2×$SCH_3$), 48.2 (C-8), 55.4 ($OCH_3$), 102.9 (C-6), 110.4 (C-3), 113.7 (C-4), 117.2 (C-9), 120.8 (C-2), 124.0 (C-5), 124.9 (C-7a), 128.0 (C-3a), 146.1 (C-7).

EXAMPLE 5

Single Crystal X-Ray Analysis of Dithyreanitrile

Crystals suitable for analysis by single crystal X-ray diffraction were grown by slow evaporation of an ethanol solution. A crystal of approximate dimensions 0.8×0.5×0.4 mm was fixed to a glass fiber with epoxy glue, fitted into a goniometer head, and optically aligned on a computer-controlled, four-circle diffractometer (Nicolet $P2_1$). The crystals displayed monoclinic symmetry and accurate lattice parameters of $a=10.747(2)$, $b=9.864(2)$, $c=13.513(2)$ Å, and $\beta=107.83(7)°$ were determined from a least-squares fit of fifteen reflections with $2\theta$ values between 35° and 40°. Systematic extinctions (h0l, h+l=2n obsd. and OkO, k=2n obsd.) uniquely determined space group $P2_1/n$. A calculated and approximately measured density of 1.36 g/cc indicated that one molecule of composition $C_{13}H_{14}N_2OS_2$ formed the asymmetric unit. Crystallizing in space group $P2_1/n$ requires that dithyreanitrile be achiral or a racemate.

All unique diffraction maxima with $2\theta \leqq 114°$ were collected at room temperature using graphite monochromated Cu K$\alpha$ radiation (1.54178 Å), 1° $\omega$-scans, and backgrounds of 50% of the scan time on either side of the scan. A total of 2213 reflections were measured in this fashion and merged ($R_m=0.048$) to give 1833 unique reflections. Systematically monitored check reflections showed no crystal or instrumental instability, and no corrections for absorption were made. After correction for Lorentz and background effects, 1207 (66%) of the measured reflections were considered observed, i.e. $|F_o| \geqq 3\sigma(F_o)$.

An initial model of the natural product was found by a direct methods phasing approach. This model was extended with Fourier electron density syntheses and difference electron density syntheses. When all nonhydrogen atoms were located, least-squares refinement was carried out to optimize atomic coordinates. Hydrogens were included at ideal geometries and fixed. The final least-squares agreement factor was 5.20% for the observed reflections.

Final atomic coordinates and equivalent isotropic thermal parameters are given in Table V, interatomic distances are given in Table VI, interatomic angles are given in Table VII, and torsional angles are given in Table VIII.

All crystallographic calculations were done on a PRIME 9950 computer operated by the Cornell Chemistry Computing Facility. Principal programs employed were: FOBS86, by G. Van Duyne, Cornell University, 1986; MULTAN 80 and RANTAN 80, by P. Main, S. E. Hull, L. Lessinger, G. Germain, J. P. Declercq, and M. M. Woolfson, University of York, England, 1980; DIRDIF, by P. T. Beurskens et al., University of Nijmegen, Netherlands, 1981; MITHRIL, by C. J. Gilmore, University of Glasgow, Scotland, 1983; SHELXS, by G. Sheldrick, University of Goettingen, 1986; PATSEE, by E. Egert, University of Goettingen, 1986; BLS78A, by K. Hirotsu and E. Arnold, Cornell University, 1980; CRYSTALS, by D. J. Watkin and J. R. Carruthers,

TABLE V

Fractional Coordinates and Thermal Parameters for Dithyreanitrile
Estimated standard deviations of the least-significant figures are given in parentheses. The isotropic equivalent thermal parameter is given for anisotropic atoms (denoted by an asterisk).

| Atom | x | y | z | B |
|---|---|---|---|---|
| S1 | 0.5562(1) | 0.2350(1) | 0.9744(1) | 5.6* |
| S2 | 0.8177(1) | 0.1143(1) | 1.0105(1) | 6.4* |
| 01 | 0.9653(3) | 0.7762(3) | 1.1301(2) | 6.5(1)* |
| N1 | 0.8640(4) | 0.5877(4) | 0.9657(3) | 5.1(1)* |
| N2 | 0.6545(4) | 0.2224(4) | 0.7420(3) | 6.8(1)* |
| C7a | 0.8684(4) | 0.5680(5) | 1.0679(3) | 4.8(1)* |
| C3a | 0.8149(4) | 0.4423(5) | 1.0775(3) | 4.7(1)* |
| C9 | 0.6807(5) | 0.2327(5) | 0.8293(3) | 5.5(1)* |
| C3 | 0.7760(4) | 0.3834(4) | 0.9749(3) | 4.7(1)* |

TABLE V-continued

Fractional Coordinates and Thermal Parameters for Dithyreanitrile
Estimated standard deviations of the least-significant figures are given in parentheses. The isotropic equivalent thermal parameter is given for anisotropic atoms (denoted by an asterisk).

| Atom | x | y | z | B |
|---|---|---|---|---|
| C4 | 0.8076(5) | 0.4006(5) | 1.1751(3) | 5.6(2)* |
| C6 | 0.9070(5) | 0.6150(5) | 1.2467(3) | 6.0(2)* |
| C2 | 0.8086(4) | 0.4757(5) | 0.9109(3) | 5.1(1)* |
| C7 | 0.9160(4) | 0.6561(6) | 1.1522(3) | 5.7(2)* |
| C5 | 0.8533(5) | 0.4879(5) | 1.2573(3) | 6.2(2)* |
| C8 | 0.7102(4) | 0.2494(4) | 0.9424(3) | 4.9(1)* |
| C10 | 0.4590(5) | 0.3633(6) | 0.8921(4) | 7.1(2)* |
| C12 | 1.0099(6) | 0.8711(6) | 1.2134(4) | 7.8(2)* |
| C11 | 0.7307(6) | −0.0345(6) | 0.9500(4) | 8.0(2)* |
| HN1 | 0.8960 | 0.6699 | 0.9369 | 6.7 |
| H4 | 0.7693 | 0.3086 | 1.1850 | 6.7 |
| H6 | 0.9401 | 0.6732 | 1.3121 | 6.7 |
| H2 | 0.7964 | 0.4615 | 0.8354 | 6.7 |
| H5 | 0.8484 | 0.4629 | 1.3290 | 6.7 |
| H10a | 0.4493 | 0.3400 | 0.8152 | 6.7 |
| H10b | 0.5020 | 0.4534 | 0.9065 | 6.7 |
| H10c | 0.3698 | 0.3668 | 0.8988 | 6.7 |
| H12a | 0.0827 | 0.8291 | 1.2736 | 6.7 |
| H12b | 0.9374 | 0.8975 | 1.2424 | 6.7 |
| H12c | 0.0465 | 0.9551 | 1.1913 | 6.7 |
| H11a | 0.7204 | −0.0354 | 0.8750 | 6.7 |
| H11b | 0.6437 | −0.0383 | 0.9622 | 6.7 |
| H11c | 0.7826 | −0.1182 | 0.9836 | 6.7 |

TABLE VI

Interatomic Distances for Dithyreanitrile
An estimated standard deviation of the least-significant figures for each distance is given in parentheses.

| | | | | | |
|---|---|---|---|---|---|
| S1 - C8 | 1.840(7) | S1 - C10 | 1.794(19) | S2 - C8 | 1.818(18) |
| S2 - C11 | 1.797(17) | 01 - C7 | 1.368(10) | 01 - C12 | 1.429(14) |
| N1 - C7a | 1.381(6) | N1 - C2 | 1.361(13) | N1 - HN1 | 1.004(7) |
| N2 - C9 | 1.131(7) | C7a - C3a | 1.390(11) | C7a - C7 | 1.399(13) |
| C3a - C3 | 1.442(11) | C3a - C4 | 1.406(8) | C9 - C8 | 1.471(8) |
| C3 - C2 | 1.372(11) | C3 - C8 | 1.501(13) | C4 - C5 | 1.373(13) |
| C4 - H4 | 1.022(8) | C6 - C7 | 1.371(9) | C6 - C5 | 1.406(11) |
| C6 - H6 | 1.023(10) | C2 - H2 | 0.997(5) | C5 - H5 | 1.016(6) |
| C10 - H10a | 1.038(6) | C10 - H10b | 0.993(9) | C10 - H10c | 0.990(6) |
| C12 - H12b | 1.008(9) | C11 - H11a | 0.985(6) | C11 - H11b | 0.998(8) |
| C11 - H11c | 1.022(11) | | | | |

TABLE VII

Interatomic Angles for Dithyreanitrile
An estimated standard deviation of the least-significant figures for each angle is given in parentheses.

| | | | |
|---|---|---|---|
| C8 - S1 - Cl0 | 101.2(3) | C8 - S2 - C11 | 101.9(5) |
| C7 - 01 - C12 | 117.1(3) | C7a - N1 - C2 | 107.8(3) |
| C7a - N1 - HNl | 126.1(3) | C2 - N1 - HN1 | 126.1(3) |
| Nl - C7a - C3a | 109.3(5) | N1 - C7a - C7 | 106.0(4) |
| C3a - C7a - 7 | 122.5(3) | C7a - C3a - C3 | 106.0(4) |
| C7a - C3a - C4 | 119.5(4) | C3 - C3a - C4 | 134.5(3) |
| N2 - C9 - C8 | 177.8(3) | C3a - C3 - C2 | 106.5(3) |
| C3a - C3 - C8 | 127.4(4) | C2 - C3 - C8 | 126.0(4) |
| C3a - C4 - C5 | 117.8(3) | C7 - C6 - C5 | 120.5(5) |
| Nl - C2 - C3 | 110.4(4) | 01 - C7 - C7a | 115.5(3) |
| 01 - C7 - C6 | 127.0(4) | C7a - C7 - C6 | 117.5(4) |
| C4 - C5 - C6 | 122.2(5) | S1 - C8 - S2 | 107.6(3) |
| S1 - C8 - C9 | 108.2(4) | S1 - C8 - C3 | 112.1(3) |
| S2 - C8 - C9 | 110.2(5) | S2 - C8 - C3 | 109.2(5) |
| C9 - C8 - C3 | 109.6(4) | | |

TABLE VIII

Torsional Angles for Dithyreanitrile
An estimated standard deviation of the least-significant figures for each angle is given in parentheses.

| | | | |
|---|---|---|---|
| C10 - S1 - CB - S2 | −174.7(2) | C10 - S1 - C8 - C9 | −55.7(7) |
| C10 - S1 - C8 - C3 | 65.2(6) | C11 - S2 - C8 - S1 | 64.7(6) |
| C11 - S2 - C8 - C9 | −53.0(7) | C11 - S2 - C8 - C3 | −173.4(4) |
| C12 - 01 - C7 - C7a | 177.5(4) | C12 - 01 - C7 - C6 | −1.5(7) |
| C2 - N1 - C7a - C3a | −0.1(5) | C2 - N1 - C7a - C7 | −179.4(5) |

TABLE VIII-continued

Torsional Angles for Dithyreanitrile
An estimated standard deviation of the least-significant figures for each angle is given in parentheses.

| | | | |
|---|---|---|---|
| HN1 - N1 - C7a - C3a | 179.9(4) | HN1 - N1 - C7a - C7 | 0.6(8) |
| C7a - N1 - C2 - C3 | 0.3(5) | HN1 - N1 - C2 - C3 | −179.7(4) |
| N1 - C7a - C3a - C3 | −0.1(5) | N1 - C7a - C3a - C4 | −179.3(4) |
| C7 - C7a - C3a - C3 | 179.3(4) | C7 - C7a - C3a - C4 | 0.0 |
| N1 - C7a - C7 - 01 | −0.6(7) | N1 - C7a - C7 - C6 | 178.5(5) |
| C3a - C7a - C7 - 01 | −179.8(4) | C3a - C7a - C7 - C6 | −0.7(7) |
| C7a - C3a - C3 - C2 | 0.3(5) | C7a - C3a - C3 - C8 | −178.5(4) |
| C4 - C3a - C3 - C2 | 179.4(5) | C4 - C3a - C3 - C8 | 0.6(8) |
| C7a - C3a - C4 - C5 | 0.6(7) | C3 - C3a - C4 - C5 | −178.4(5) |
| N2 - C9 - C8 - S1 | 41.5(135) | N2 - C9 - C8 - S2 | 158.9(133) |
| M2 - C9 - C8 - C3 | −81.0(135) | C3a - C3 - C2 - N1 | −0.3(5) |
| C8 - C3 - C2 - N1 | 178.4(4) | C3a - C3 - C8 - S1 | 56.3(8) |
| C3a - C3 - C8 - S2 | −62.8(8) | C3a - C3 - C8 - C9 | 176.5(4) |
| C2 - C3 - C8 - S1 | −122.1(8) | C2 - C3 - C8 - S2 | 118.7(7) |
| C2 - C3 - C8 - C9 | −2.1(6) | C3a - C4 - C5 - C6 | −0.5(7) |
| C5 - C6 - C7 - 01 | 179.8(5) | C5 - C6 - C7 - C7a | 0.8(7) |
| C7 - C6 - C5 - C4 | −0.2(8) | | |

Oxford University, 1981; ORTEP, by C. K. Johnson, Oak Ridge National Laboratory, 1970; PL1PLOT, by G. Van Duyne, Cornell University, 1984; TABLES, by G. Van Duyne, Cornell University, 1986.

EXAMPLE 6

Materials and Instrumentation $^{1}$H NMR spectra were taken on either a Varian XL-200 or XL-400 spectrometer. $^{13}$C NMR spectra were taken on a Varian XL-400 spectrometer. IR spectra were taken on either a Perkin-Elmer 299B or a Mattson Polaris FT-IR spectrophotometer. Mass spectra were taken on either a Finnigan 3300 or an AEI MS-902 mass spectrometer. Hydrogenations were carried out on a Series 3910 Parr Hydrogenator. Trimethylsilyl cyanide (98%), boron trifluoride etherate (purified and redistilled), and tin (IV) chloride (anhydrous, 99%) were obtained from Aldrich Chemical Company. Methylthiotrimethylsilane (approximately 95%) was obtained from Fluka. Silica gel (approximately 40 μm average particle diameter) was obtained from J. T. Baker Chemical Company. A reaction run under dry conditions signifies a reaction run in flame- or oven-dried glassware and under an argon or nitrogen atmosphere.

EXAMPLE 7

3-Methoxy-2,β-dinitrostyrene (2)

Compound 2 was prepared according to the procedure of A. Kalir et al. [Isr. J. Chem. 5: 129–136 (1967)]. To a 100-mL round bottom flask, 6.674 g of powdered 3-methoxy-2-nitrobenzaldehyde (98%, Aldrich) (36.87 mmol), 2.1 mL of nitromethane (39 mmol), and 15.5 mL of methanol were added. This suspension was cooled to approximately 5° C., and 5.6 mL of 9.5N aqueous sodium hydroxide (53 mmol) was added. An additional 1 mL of nitromethane, 9.5N aqueous sodium hydroxide, and methanol was added. The reaction mixture was stirred for 1 hr at approximately 5° C. Over the course of the hour an additional 5 mL of methanol was added. After 1 hr the precipitate was dissolved in 25 mL of water. This solution was added to 20 mL of 10% aqueous hydrochloric acid. The resulting precipitate was extracted with three 100-mL portions, one 50-mL portion, and finally one 25-mL portion of diethyl ether. The ether extracts were combined, dried with $MgSO_4$, and filtered. The ether was removed by rotary evaporation and the residue was refluxed for 5 min in 31 mL of acetic anhydride and 3.566 g of anhydrous sodium acetate. The solution was allowed to cool and then was diluted with water. The precipitate was collected. Recrystallization from hot methanol with a recovery of a second crop of crystals from the mother liquor yielded 5.891 g (71%) of 2 as yellow crystals: $^{1}$H NMR ($CDCl_3$) δ 3.94 (s, 3H, $OCH_3$), 7.19 (d, 2H, J=8.3 Hz), 7.50 (m, 2H), 7.85 (d, 1H, J=13.7 Hz).

EXAMPLE 8

7-Methoxyindole (3)

Compound 3 was synthesized according to the procedure of A. Kalir et al. [supra]. To a 250-mL Parr hydrogenation bottle, 4.893 g of 2 (21.84 mmol) was added. Compound 2 was dissolved in 90 mL of hot ethyl acetate and 9.0 mL of acetic acid. To this solution 0.260 g of 10% palladium on activated carbon (Aldrich) was added. This mixture was hydrogenated overnight at 4 atm. When the pressure stabilized, the reaction mixture was filtered and the solvent removed by rotary evaporation. The residue was dissolved in 60 mL of diethyl ether. The ether solution was washed with 35 mL of 5% aqueous ammonium hydroxide, 5% aqueous hydrochloric acid, and water, dried with $MgSO_4$, and filtered. The ether was removed by rotary evaporation to yield 2.009 g of a green oil. This oil was chromatographed over 85 g of silica gel with 6:1 hexanes:ethyl acetate to yield 1.863 g (58%) of 3 as a very pale yellow oil: $^{1}$H NMR ($CDCl_3$) δ 3.99 (s, 3H, $OCH_3$), 6.61 (m, 2H), 7.18 (m, 3H), 8.43 (br s, 1H, NH).

EXAMPLE 9

3-(7-Methoxy)-indolyl Trifluoromethyl Ketone (4)

The synthesis of 4 was a modification of a procedure for the preparation of 3-indolyl trifluoromethyl ketone by R. K. Mackie et al. [J. Fluorine Chem. 10: 437–445 (1977)]. Under dry conditions, 4.6 mL of trifluoroacetic anhydride (99+%, Aldrich) (33 mmol) and 41 mL of anhydrous diethyl ether were placed in a 100-mL round bottom flask and cooled to approximately −5° C. A solution of 1.936 g of 3 (13.17 mmol) in 7 mL of anhydrous diethyl ether was added to the cooled trifluoroacetic anhydride solution. The reaction mixture was stirred for 6 hr at approximately −5° C. After 6 hr the reaction mixture was washed with three 26-mL portions of saturated aqueous sodium bicarbonate and then three 26-mL portions of water. The aqueous washes were combined and extracted with three 30-mL portions of diethyl ether. The ether extracts were combined, dried with $Na_2SO_4$, and filtered. The ether was removed by rotary evaporation to yield 3.060 g (96%) of 4 as a yellow solid: $^{1}H$ NMR ($CDCl_3$) δ 3.98 (s, 3H, $OCH_3$), 6.80 (d, 1H, J=7.9 Hz), 7.28 (app. t, 1H, J=8 Hz), 7.98 (m, 2H), 9.10 (br s, 1H, NH).

EXAMPLE 10

7-Methoxyindole-3-carboxylic acid (5)

Preparation of 5 was based on a procedure for the synthesis of indole-3-carboxylic acid reported by R. K. Mackie et al. [supra]. To a 200-mL round bottom flask, 2.369 g of 4 (9.75 mmol) was added. Compound 4 was dissolved in 19 mL of absolute ethanol and 53 mL of 5N aqueous sodium hydroxide, refluxed overnight, and allowed to cool. The ethanol was removed by rotary evaporation, and the resulting solution was extracted with two 25-mL portions of diethyl ether. The aqueous solution was acidified with concentrated hydrochloric acid, and the peach-colored precipitate was collected. Recrystallization from hot aqueous ethanol (50:50 ethanol:water) yielded 0.883 g (47%) of 5 as cream-colored crystals: $^{1}H$ NMR (acetone-$d_6$) δ 3.95 (s, 3H, $OCH_3$), 6.76 (d, 1H, J=7.3 Hz), 7.10 (app. t, 1H, J=8 Hz), 7.71 (d, 1H, J=8.5 Hz), 7.95 (m, 1H), 11.0 (br s, 1H).

EXAMPLE 11

Dithyreanitrile (8)

The natural product was synthesized from 5 without isolation of 6 or 7 [Richardson et al., DE 3 429 830 (1985); Olah et al., Synthesis, 636–637 (1983); Evans et al., J. Am. Chem. Soc. 99: 5009–5017 (1977)]. Under dry conditions 0.555 g of 5 (2.91 mmol) and 25 mL of methylene chloride, freshly distilled from phosphorus pentoxide under nitrogen, were added to a 50-mL round bottom flask. To this suspension, 0.41 mL of oxalyl chloride (99+%, Aldrich) (4.7 mmol) was added dropwise and gas evolution began. The reaction mixture was stirred overnight at room temperature.

On completion of the reaction, as judged by TLC, dissolution of 5, and cessation of bubbling, 0.65 mL of trimethylsilyl cyanide (4.9 mmol) was added to the reaction mixture. The reaction mixture was stirred at room temperature overnight.

After stirring overnight the solution was concentrated to a volume of 5 mL, and 20 mL of anhydrous diethyl ether was added. To this dark purple solution, 1.5 mL of methylthiotrimethylsilane (11 mmol) and 0.35 mL of boron trifluoride etherate (2.8 mmol) were added. The reaction mixture was stirred at room temperature overnight. An additional 5 mL of anhydrous diethyl ether was added during this time. After stirring overnight the reaction was quenched with 15 mL of water. The aqueous layer was extracted with four 10-mL portions of diethyl ether. The ether extracts were combined, dried with $K_2CO_3$, and filtered. The solvent was removed by rotary evaporation to yield 0.813 g of crude material. This material was chromatographed over 53 g of silica gel with 5:1 hexanes:ethyl acetate to yield 0.102 g (13%) of 8 as a white solid: $^{1}H$ NMR ($CDCl_3$) δ 2.28 (s, 6H, 2×$SCH_3$), 3.96 (s, 3H, $OCH_3$), 6.69 (d, 1H, J=7.8 Hz), 7.09 (app. t, 1H, J=8 Hz), 7.45 (d, 1H, J=2.7 Hz), 7.66 (d, 1H, J=8.2 Hz), 8.45 (br s, 1H, NH); IR ($CCl_4$) (partial) 3480, 2230, 1580, 1500, 1415 $cm^{-1}$; $^{13}C$ NMR ($CDCl_3$) δ 15.7, 48.2, 55.4, 102.9, 110.2, 113.6, 117.2, 120.8, 124.0, 124.9, 127.9, 146.2. Both the TLC and the spectroscopic data of 8 were identical to those of the isolated natural product.

EXAMPLE 12

Compound 9

The synthesis of 9 was a modification of the procedure for the preparation of 8. Compound 9 was synthesized from indole-3-carboxylic acid without characterization of either indole-3-carbonyl chloride or indole-3-carbonyl cyanide. Under dry conditions, 0.527 g of indole-3-carboxylic acid (99%, Aldrich) (3.27 mmol), 14 mL of anhydrous diethyl ether, and 1.0 mL of thionyl chloride (99+%, Aldrich) (14 mmol) were added to a two-neck 25-mL round bottom flask. This solution was then refluxed for 7 hr. After 7 hr the reaction mixture was transferred to a 50-mL round bottom flask. The ether and thionyl chloride were removed by rotary evaporation to yield a pink solid, which gradually turned to a pale purple solid on standing.

Under dry conditions, the pink-purple solid was dissolved in 20 mL of methylene chloride freshly distilled from phosphorus pentoxide under nitrogen. To the pale purple solution, 0.50 mL of trimethylsilyl cyanide (3.7 mmol) was added dropwise. On addition of the trimethylsilyl cyanide, the color of the solution changed from pale purple to bronze. The reaction mixture was stirred for 4 days at room temperature. After 4 days the methylene chloride was evaporated and 30 mL of anhydrous diethyl ether was added. The solution was filtered into a 50-mL round bottom flask, and the ether was removed by rotary evaporation to yield a beige solid.

Under dry conditions, the majority of the beige solid was dissolved in 30 mL of anhydrous diethyl ether. To this solution 2.0 mL of methylthiotrimethylsilane (14 mmol) and 0.40 mL of boron trifluoride etherate (3.3 mmol) were added. The reaction mixture was stirred overnight at room temperature. After this time period the reaction was quenched with 15 mL of water. The aqueous portion was extracted with two 15-mL portions of diethyl ether. The ether extracts were combined, dried with $K_2CO_3$, and filtered. The ether was removed by rotary evaporation to yield 0.716 g of crude material. This material was chromatographed over 50 g of silica gel with 4:1 hexanes:ethyl acetate to yield 0.180 g (22%) of 9 as a pale yellow solid: $^{1}H$ NMR ($CDCl_3$) δ 2.28 (s, 6H, 2×$SCH_3$), 7.35 (m, 4H), 8.10 (d, 1H, J=7.9 Hz) 8.25 (br s, 1H, NH); IR ($CHCl_3$) (partial) 3470, 2990, 2925, 2230, 1535, 1459, 1435, 1415 $cm^{-1}$; EI mass spectrum, m/e (relative intensity) 248 (0.3), 201 (100.0); CI mass spectrum, m/e (relative intensity) 249 (21.3), 222 (16.6), 201 (100.0).

EXAMPLE 13

Compound 10

The synthesis of 10 was a modification of the procedure for the preparation of 8. It was previously reported by Marchand et al. [supra]. Under dry conditions, 1.362 g of benzoyl cyanide (98%, Aldrich) (10.4 mmol), 15 mL of anhydrous diethyl ether, 1.28 mL of boron trifluoride etherate (10.4 mmol), and 6.6 mL of methylthiotrimethylsilane (47 mmol) were added to a 50-mL round bottom flask. This solution was stirred for 1 hr at room temperature, then refluxed for 1 week, and finally stirred at room temperature for 2 days. After this time period the reaction was quenched with 15 mL of water and 10 mL of diethyl ether. The aqueous portion was extracted with three 10-mL portions of diethyl ether. The ether extracts were combined, dried with $K_2CO_3$, and filtered. The ether was removed by rotary evaporation to yield 2.033 g of crude material. This material was chromatographed over 125 g of silica gel with 50:1 hexanes:ethyl acetate to yield 1.096 (50%) of 10 as a colorless oil which solidified on standing in the freezer: $^1$H NMR ($CDCl_3$) δ 2.29 (s, 6H, 2×$SCH_3$), 7.41 (m, 3H), 7.73 (m, 2H); IR ($CCl_4$) (partial) 3065, 2990, 2925, 2230, 1598, 1498, 1489, 1450, 1435, 1422 $cm^{-1}$; $^{13}$C NMR ($CDCl_3$) δ 16.2, 53.8, 117, 127.1, 129.2, 129.7, 135.3; EI mass spectrum m/e (relative intensity) 209 (1.59), 162 (100.0); CI mass spectrum, m/e (relative intensity) 210 (51.43), 183 (100.0), 163 (99.42), 162 (85.49).

EXAMPLE 14 p-Toluoyl Cyanide p-Toluoyl cyanide was prepared according to the general procedure reported by Olah et al. [supra]. Under dry conditions, 1.35 mL of p-toluoyl chloride (98%, Aldrich) (10.2 mmol), 26 mL of methylene chloride, freshly distilled from phosphorus pentoxide under nitrogen, and 1.53 mL of trimethylsilyl cyanide (11.5 mmol) were added to a 100-mL round bottom flask. To this solution 0.25 mL of tin (IV) chloride (2.1 mmol) was added. This mixture was stirred for 2 hr at room temperature. During the 2 hr, the color of the solution changed from pale yellow to dark brown. After 2 hr the reaction mixture was quenched with 75 mL of ice-cold water and then extracted with two 75-mL portions of methylene chloride. The methylene chloride extracts were combined, washed with two 75-mL portions of ice-cold water, dried with $MgSO_4$, and filtered. The methylene chloride was removed by rotary evaporation to yield a dark brown oil which solidifed on standing. This crude product was dissolved in hexanes and filtered. The solvent was removed by rotary evaporation to yield 1.266 g (86%) of p-toluoyl cyanide as a yellow solid: IR ($CCl_4$) (partial) 2220, 1685, 1607 $cm^{-1}$.

EXAMPLE 15

Compound 11

The synthesis of 11 was a modification of the procedure for the preparation of 8. Under dry conditions, 1.266 g of p-toluoyl cyanide (8.73 mmol), 22 mL of anhydrous diethyl ether, 1.1 mL of boron trifluoride etherate (8.9 mmol), and 5.1 mL of methylthiotrimethylsilane (36 mmol) were added to a 100-mL round bottom flask. The reaction mixture was refluxed for 4 days. After 4 days the reaction was quenched with 15 mL of water and 15 mL of diethyl ether. The aqueous portion was extracted with three 10-mL portions of diethyl ether. The ether extracts were combined, dried with $K_2CO_3$, and filtered. The ether was removed by rotary evaporation to yield 1.894 g of crude material. This material was chromatographed over 125 g of silica gel with 50:1 hexanes:ethyl acetate to yield 1.255 g (64%) of 11 as a pale yellow solid: $^1$H NMR ($CDCl_3$) δ 2.28 (s, 6H, 2×$SCH_3$), 2.36 (s, 3H, $CH_3$), 7.21 (d, 2H, J=8.2 Hz), 7.61 (d, 2H, J=8.2 Hz); IR ($CCl_4$) (partial) 3030, 2990, 2925, 2230, 1509, 1435, 1421 $cm^{-1}$.

EXAMPLE 16

2-Fluorobenzoyl Cyanide

2-Fluorobenzoyl cyanide was prepared according to the general procedure reported by G. A. Olah et al. [supra]. Under dry conditions, 1.2 mL of 2-fluorobenzoyl chloride (97%, Aldrich) (10 mmol), 26 mL of methylene chloride, freshly distilled from phosphorus pentoxide under nitrogen, and 1.55 mL of trimethylsilyl cyanide (12 mmol) were placed in a 100-mL round bottom flask. To this solution 0.25 mL of tin (IV) chloride (2.1 mmol) was added. On addition of the tin (IV) chloride, the color of the solution changed from yellow to dark brown. The reaction mixture was stirred for 2 hr at room temperature, then quenched with 75 mL of ice-cold water, and finally extracted with two 75-mL portions of methylene chloride. The methylene chloride extracts were combined, washed with two 75-mL portions of ice-cold water, dried with $MgSO_4$, and filtered. The methylene chloride was removed by rotary evaporation to yield a dark brown oil which was purified by Kugelrohr vacuum distillation to yield 0.711 g (47%) of 2-fluorobenzoyl cyanide as a colorless oil: IR ($CH_2Cl_2$) (partial) 2225, 1695, 1670, 1610, 1489, 1484, 1457 $cm^{-1}$.

EXAMPLE 17

Compound 12

The synthesis of 12 was a modification of the procedure for the preparation of 8. Under dry conditions, 0.711 g of 2-fluorobenzoyl cyanide (4.77 mmol), 18 mL of anhydrous diethyl ether, 0.59 mL of boron trifluoride etherate (4.8 mmol), and 3.0 mL of methylthiotrimethylsilane (21 mmol) were added to a 50-mL round bottom flask. This solution was refluxed for 3 days. After this time period the reaction was quenched with 15 mL of water and 10 mL of diethyl ether. The aqueous portion was extracted with two 10-mL portions of diethyl ether. The ether extracts were combined, dried with $K_2CO_3$, and filtered. The ether was removed by rotary evaporation to yield 1.071 g of crude material. This material was chromatographed over 60 g of silica gel with 20:1 hexanes:ethyl acetate to yield 0.841 g (78%) of 12 as a colorless oil that solidified on standing in the freezer: $^1$H NMR ($CDCl_3$) δ 2.35 (s, 6H, 2×$SCH_3$), 7.19 (m, 2H), 7.41 (m, 1H), 7.80 (m, 1H); IR ($CCl_4$) (partial) 2930, 2230, 1613, 1493, 1485, 1458, 1436, 1421 $cm^{-1}$.

EXAMPLE 18

4-Fluorobenzoyl Cyanide

4-Fluorobenzoyl cyanide was prepared according to the general procedure reported by G. A. Olah et al. [supra]. Under dry conditions, 1.829 g of 4-fluorobenzoyl chloride (98%, Aldrich) (11.54 mmol), 30 mL of methylene chloride, freshly distilled from phosphorus pentoxide under nitrogen, and 1.8 mL of trimethylsilyl cyanide (13 mmol) were added to a 100-mL round bottom flask. To this solution 0.29 mL of tin (IV) chloride (2.5 mmol) was added. On addition of the tin (IV) chloride, the color of the solution changed from clear to dark yellow and within 5 min the color of the solution was dark brown. The reaction mixture was stirred for 2 hr at room temperature, then quenched with 90 mL of ice-cold water, and finally extracted with two 90-mL portions of methylene chloride. The methylene chloride extracts were combined, washed with two 90-mL portions of ice-cold water, dried with $MgSO_4$, and filtered. The methylene chloride was removed by rotary evaporation. The dark brown residue which resulted was stirred with pentane. The pentane solution was decanted and the pentane removed by rotary evaporation to yield 0.911 g of 4-fluorobenzoyl cyanide as a yellow oil. The product was further purified by Kugelrohr vacuum distillation which afforded 0.666 g (39%) of 4-fluorobenzoyl cyanide as a colorless oil that solidified on standing in the freezer: IR ($CCl_4$) (partial) 2220, 1685, 1600, 1505, 1410 $cm^{-1}$.

EXAMPLE 19

Compound 13

The synthesis of 13 was a modification of the procedure for the preparation of 8. Under dry conditions, 0.4212 g of 4-fluorobenzoyl cyanide (2.83 mmol), 20 mL of anhydrous diethyl ether, 1.7 mL of methylthiotrimethylsilane (12 mmol), and 0.35 mL of boron trifluoride etherate (2.8 mmol) were added to a three-neck 50-mL round bottom flask. The mixture was refluxed for 4 days, over which time additional anhydrous diethyl ether was added in order to maintain the volume of the solution. After 4 days of reflux the reaction mixture was quenched with 10 mL of diethyl ether and 10 mL of water. The aqueous portion was extracted with three 7-mL portions of diethyl ether. The ether extracts were combined, dried with $K_2CO_3$, and filtered. The ether was removed by rotary evaporation to yield 0.667 g of a dark yellow oil. This oil was chromatographed over 33 g of silica gel with 20:1 hexanes:ethyl acetate to yield 0.436 g (68%) of 13 as a yellow oil: $^1H$ NMR ($CDCl_3$) $\delta$ 2.27 (s, 6H, 2×$SCH_3$), 7.08 (m, 2H), 7.72 (m, 2H); IR ($CCl_4$) (partial) 2920, 2230, 1890, 1600, 1510, 1435, 1420 $cm^{-1}$.

EXAMPLE 20 p-Anisoyl Cyanide p-Anisoyl cyanide was prepared according to the general procedure reported by G. A. Olah et al. [supra]. Under dry conditions, 1.8740 g of p-anisoyl chloride (99%, Aldrich) (10.98 mmol), 30 mL of methylene chloride, freshly distilled from phosphorus pentoxide under nitrogen, and 1.7 mL of trimethylsilyl cyanide (13 mmol) were added to a 100-mL round bottom flask. To this solution, 0.27 mL of tin (IV) chloride (2.3 mmol) was added. The reaction was stirred for 2 hr at room temperature. During the 2 hr, the color of the solution changed from clear to dark brown. After the 2 hr of stirring, the reaction was quenched with 75 mL of ice-cold water and then extracted with two 75-mL portions of methylene chloride. The methylene chloride extracts were combined, washed with two 75-mL portions of ice-cold water, dried with $MgSO_4$, and filtered. The methylene chloride was removed by rotary evaporation to yield 1.592 g (90%) of p-anisoyl cyanide as a dark orange solid: IR ($CHCl_3$) (partial) 3020, 2220, 1675, 1600 $cm^{-1}$.

EXAMPLE 21

Compound 14

The synthesis of 14 was a modification of the procedure for the preparation of 8. Under dry conditions, 1.2514 g of p-anisoyl cyanide (7.77 mmol), 29 mL of anhydrous diethyl ether, 4.3 mL of methylthiotrimethylsilane (30 mmol), and 0.96 mL of boron trifluoride etherate (7.8 mmol) were added to a three-neck 100-mL round bottom flask. The mixture was refluxed for 4 days and then quenched with 15 mL of water and 10 mL of diethyl ether. The aqueous portion was extracted with three 10-mL portions of diethyl ether. The ether extracts were combined, dried with $K_2CO_3$, and filtered. The ether was removed by rotary evaporation to yield 1.847 g of an orange oil. This oil was chromatographed over 94 g of silica gel with 20:1 hexanes:ethyl acetate to yield 1.0145 g of a very pale yellow oil. This oil was rechromatographed over silica gel with 5:1 methylene chloride:hexanes to yield 0.748 g (40%) of 14 as a white solid: $^1H$ NMR ($CDCl_3$) $\delta$ 2.26 (s, 6H, 2×$SCH_3$), 3.82 (s, 3H, $OCH_3$), 6.91 (d, 2H, J=8.8 Hz), 7.64 (d, 2H, J=8.8 Hz); IR ($CCl_4$) (partial) 2230, 1610, 1510 $cm^{-1}$.

EXAMPLE 22 m-Anisoyl Cyanide m-Anisoyl cyanide was prepared according to the general procedure reported by G. A. Olah et al. [supra]. Under dry conditions, 1.686 g of m-anisoyl chloride (99%, Aldrich) (9.88 mmol), 30 mL of methylene chloride, freshly distilled from phosphorus pentoxide under nitrogen, and 1.6 mL of trimethylsilyl cyanide (12 mmol) were added to a 100-mL round bottom flask. To this solution 0.25 mL of tin (IV) chloride (2.1 mmol) was added. On addition of the tin (IV) chloride, the color of the solution changed from pale bronze to dark yellow. The solution was stirred for 2 hr at room temperature. After 2 hr of stirring the color of the solution was dark brown. The reaction mixture was quenched with 75 mL of ice-cold water and then extracted with two 75-mL portions of methylene chloride. The methylene chloride extracts were combined, washed with two 75-mL portions of ice-cold water, dried with $MgSO_4$, and filtered. The methylene chloride was evaporated to yield 1.506 g of a dark brown oil. This oil was stirred with hot pentane. The pentane solution was decanted and the pentane was removed by rotary evaporation to yield 1.238 g (78%) of m-anisoyl cyanide as a yellow oil: IR ($CCl_4$) (partial) 2230, 1690 $cm^{-1}$.

EXAMPLE 23

Compound 15

The synthesis of 15 was a modification of the procedure for the preparation of 8. Under dry conditions, 1.179 g of m-anisoyl cyanide (7.32 mmol), 27 mL of anhydrous diethyl ether, 3.6 mL of methylthiotrimethylsilane (25 mmol), and 0.90 mL of boron trifluoride etherate (7.3 mmol) were added to a three-neck 100-mL round bottom flask. The reaction mixture was refluxed for 2 days and then quenched with 15 mL of water and 10 mL of diethyl ether. The aqueous portion was extracted with three 7-mL portions of diethyl ether. The ether extracts were combined, dried with $MgSO_4$, and filtered. The ether was removed by rotary evaporation to yield 1.783 g of an orange oil. This oil was chromatographed over 92 g of silica gel with 20:1 hexanes:ethyl acetate to yield 1.499 g (86%) of 15 as a pale yellow oil: $^1H$ NMR ($CDCl_3$) $\delta$ 2.28 (s, 6H, 2×$SCH_3$), 3.82 (s, 3H, $OCH_3$), 6.91 (m, 1H), 7.30 (m, 3H); IR ($CCl_4$) (partial) 2920, 2840, 2230, 1600, 1490, 1470, 1435 $cm^{-1}$.

EXAMPLE 24 m-Toluoyl Cyanide m-Toluoyl cyanide was prepared according to the general procedure reported by G. A. Olah et al. [supra]. Under dry conditions, 2.4170 g of m-toluoyl chloride (99%, Aldrich) (15.63 mmol), 40 mL of methylene chloride, freshly distilled from phosphorus pentoxide under nitrogen, and 2.4 mL of trimethylsilyl cyanide (18 mmol) were added to a 100-mL round bottom flask. To this solution 0.39 mL of tin (IV) chloride (3.3 mmol) was added. On addition of the tin (IV) chloride the color of the solution changed from clear to yellow. The reaction mixture was stirred for 2 hr at room temperature. After 2 hr of stirring, the color of the solution was dark brown. The reaction was quenched with 120 mL of ice-cold water and then extracted with two 120 mL portions of methylene chloride. The methylene chloride extracts were combined, washed with two 120-mL portions of ice-cold water, dried with $MgSO_4$, and filtered. The methylene chloride was removed by rotary evaporation to yield 2.125 g of a dark brown oil. This oil was distilled at 45°–48° C. (0.2 mm) to yield 1.410 g (62%) of m-toluoyl cyanide as a white solid: IR ($CCl_4$) (partial) 2220, 1685, 1600, 1580 $cm^{-1}$.

EXAMPLE 25

Compound 16

The synthesis of 16 was a modification of the procedure for the preparation of 8. Under dry conditions, 1.346 g of m-toluoyl cyanide (9.28 mmol), 27 mL of anhydrous diethyl ether, 4.8 mL of methylthiotrimethylsilane (34 mmol), and 1.0 mL of boron trifluoride etherate (8.1 mmol) were added to a three-neck 100-mL round bottom flask. The solution was refluxed for 4 days, during which time additional anhydrous diethyl ether was added in order to maintain the volume of the solution. After 4 days of reflux the reaction was quenched with 15 mL of water. The aqueous portion was extracted with three 10-mL portions of diethyl ether. The ether extracts were combined, dried with $K_2CO_3$, and filtered. The ether was removed by rotary evaporation to yield 2.192 g of a dark yellow oil. This oil was chromatographed over 102 g of silica gel with 50:1 hexanes:ethyl acetate to yield 1.671 g (81%) of 16 as a bright yellow oil that solidified on standing in the freezer: $^1H$ NMR ($CDCl_3$) δ 2.28 (s, 6H, 2×$SCH_3$), 2.38 (s, 3H, $CH_3$), 7.25 (m, 2H), 7.53 (m, 2H); IR ($CCl_4$) (partial) 2920, 2230, 1610, 1490, 1430, 1420 $cm^{-1}$.

EXAMPLE 26

4-Heptylbenzoyl Cyanide

4-Heptylbenzoyl cyanide was synthesized according to the general procedure reported by G. A. Olah et al [supra]. Under dry conditions, 2.5518 g of 4-heptylbenzoyl chloride (99%, Aldrich) (10.69 mmol), 30 mL of methylene chloride, freshly distilled from phosphorus pentoxide under nitrogen, and 1.65 mL of trimethylsilyl cyanide (12 mmol) were added to a 100-mL round bottom flask. To this solution 0.27 mL of tin (IV) chloride (2.3 mmol) was added. The reaction mixture was stirred for 2 hr at room temperature. During the 2 hr, the color of the solution changed from a pale yellow to dark brown. After 2 hr of stirring, the reaction was quenched with 81 mL of ice-cold water and then extracted with two 81-mL portions of methylene chloride. The methylene chloride extracts were combined, washed with two 81-mL portions of ice-cold water, dried with $MgSO_4$, and filtered. The methylene chloride was removed by rotary evaporation to yield 2.097 g of a dark brown oil. This oil was distilled at 106°–109.5° C. (0.2 mm) to yield 1.214 g (50%) of 4-heptylbenzoyl cyanide as a colorless oil that solidified on standing in the freezer: IR ($CCl_4$) (partial) 2930, 2860, 2220, 1680, 1610 $cm^{-1}$.

EXAMPLE 27

Compound 17

The synthesis of 17 was a modification of the procedure for the preparation of 8. Under dry conditions, 1.178 g of 4-heptylbenzoyl cyanide (5.14 mmol), 30 mL of anhydrous diethyl ether, 3.4 mL of methylthiotrimethylsilane (24 mmol), and 0.63 mL of boron trifluoride etherate (5.1 mmol) were added to a three-neck 100-mL round bottom flask. The solution was refluxed for 4 days, during which time additional anhydrous diethyl ether was added in order to maintain the volume of the solution. After 4 days of reflux the reaction was quenched with 5 ml of diethyl ether and 20 mL of water. The aqueous portion was extracted with three 10-mL portions of diethyl ether. The ether extracts were combined, dried with $MgSO_4$, and filtered. The ether was removed by rotary evaporation to yield 1.659 g of an orange oil. This oil was chromatographed over 91 g of silica gel with 50:1 hexanes:ethyl acetate to yield 1.231 g (78%) of 17 as a yellow oil that solidified on standing in the freezer: $^1H$ NMR ($CDCl_3$) δ 0.87 (m, 3H), 1.30 (m, 8H), 1.60 (m, 2H), 2.28 (s, 6H, 2×$SCH_3$), 2.61 (t, 2H, J=8 Hz), 7.20 (d, 2H, J=8.3 Hz), 7.62 (d, 2H, J=8.3 Hz); IR ($CCl_4$) (partial) 2920, 2850, 2230, 1510, 1470, 1430, 1420 $cm^{-1}$.

EXAMPLE 28

Two-Choice Leaf Disc Antifeedant Bioassay

The antifeedant bioassay was modified slightly from the procedure of K. L. Mikolajczak et al. [J. Nat. Prod. 51: 606 (1981)]. Disposable petri dishes (150×15 mm) were inverted, and a moistened filter paper disk large enough to cover the bottom was placed in each dish. Green bean leaf disks (1 cm diam.) were dipped for 5 sec. either in a 1% or a 10% (w/v) solution of the extract being tested, or in solvent (control). Solvents used for testing the *D. wislizenii* samples were hexane, chloroform, methanol, or 95% ethanol, and the choice of solvent was dependent on the solubility characteristics of particular sample. After allowing 5 min for solvent to evaporate, six sample-treated disks and six control-treated disks were arranged alternately in each petri dish around, and about 0.5 cm inward, from the circumference. Six fall armyworm larvae of roughly equal size, which had been reared on pinto bean artificial diet [H. H. Shorey and R. L. Hale, J. Econ. Entomol. 58: 522 (1965)] for 9 days posteclusion and starved overnight, were placed in the center of each petri dish and allowed to feed for 3 hr. Assays were conducted in darkness at 27° C. and 60% relative humidity in three simultaneous replicates.

The percentage of each disk eaten was estimated visually, and feeding ratios (defined as the percentage of extract-treated disks consumed divided by the percentage of control consumed) were calculated. A feeding ratio of 1.0 means that equal quantities of treated and control leaf tissue were eaten (no deterrency). A ratio of 0.5 or less was arbitrarily set as showing some definite feeding deterrency, and 0.2 or less as being indicative of strong feeding deterrency to that particular extract. When tested at the 1% concentration level, dithyreanitrile gave a feeding ratio of 0.11.

EXAMPLE 29

Two-Choice, Diet-Incorporated Antifeedant Bioassay

Pure compounds were dissolved in appropriate solvents and applied to powdered cellulose, which were then desiccated overnight to remove solvent. Cellulose powder-containing sample was then placed into a test tube (7.5 cm×1.0 cm), and the tube was filled to the 4-cm mark with liquid artificial fall armyworm diet medium (Bioserv #F9179). Test tubes were put on a Vortex-Genie mixer until the contents were thoroughly mixed. The diet-containing sample was then drawn from the test tubes into a plastic soda straw (19.8 cm×0.5 cm) to a height of 10 cm. Diet medium was allowed to gel and then was pushed out of the straws and cut into 0.5 cm sections. Two of these diet sections containing the sample to be tested were placed opposite one another in a 5-cm plastic petri dish. In the same dish, also placed opposite one another, were two sections of "control" diet that were prepared the same way, using the same solvent but containing no sample material. Each diet section was equidistant from the one next to it and approximately 0.5 cm in from the sides of the petri dish. Each straw contained enough material to set up 10 petri dishes; 5 replicates were prepared for each sample, and each sample was tested against fall armyworm larvae and European corn borer larvae. Twenty newly hatched fall armyworm larvae were placed in each of 5 petri dishes, and 20 newly hatched European corn borer larvae were placed in each of the other 5 petri dishes. Petri dishes containing insects were then placed in darkness at 27° C. for 16–20 hr; following this the dishes and contents were frozen to terminate feeding, and the number of larvae at each diet type in each dish was recorded. Feeding ratios were then determined by dividing the total number of insects on the treated diet from all the replicates by the total number of insects on the control diet from all the replicates. Significant difference levels were determined by Chi-square analysis.

Data obtained for fall armyworm are shown in Tables I and II, and for European corn borer in Tables III and IV.

We claim:

1. A compound of the formula:

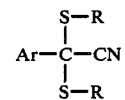

wherein R represents alkyl and Ar represents an aromatic ring selected from the group consisting of phenyl or indolyl, in each case unsubstituted, monosubstituted, or polysubstituted by identical or different substituents selected from the group consisting of halogen, alkyl, alkoxy, and halogenated alkyl; with the provision that when R is methyl, Ar is not unsubstituted phenyl.

2. A compound as described in claim 1 wherein R is methyl and Ar is 7-methyoxyindolyl-3.

3. A compound as described in claim 1 wherein R is methyl and Ar is 3-indolyl.

4. A compound as described in claim 1 wherein R is methyl and Ar is 4-methylphenyl.

5. A compound as described in claim 1 wherein R is methyl and Ar is 2-fluorophenyl.

6. A compound as described in claim 1 wherein R is methyl and Ar is 4-fluorophenyl.

7. A compound as described in claim 1 wherein R is methyl and Ar is 4-methoxyphenyl.

8. A compound as described in claim 1 wherein R is methyl and Ar is 3-methoxyphenyl.

9. A compound as described in claim 1 wherein R is methyl and Ar is 3-methylphenyl.

10. A compound as described in claim 1 wherein R is methyl and Ar is 4-n-heptylphenyl.

* * * * *